(12) United States Patent
Chang et al.

(10) Patent No.: US 7,119,331 B2
(45) Date of Patent: Oct. 10, 2006

(54) NANOPARTICLE ION DETECTION

(75) Inventors: Huan-Cheng Chang, Taipei (TW);
Wen-Ping Peng, Hou-long Town (TW);
Yong Cai, Zhengzhou (CN)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/726,071

(22) Filed: Dec. 1, 2003

(65) Prior Publication Data

US 2005/0029448 A1 Feb. 10, 2005

Related U.S. Application Data

(60) Provisional application No. 60/493,284, filed on Aug. 7, 2003.

(30) Foreign Application Priority Data

Sep. 19, 2003  (TW) .............................. 92125852 A

(51) Int. Cl.
*B01D 59/44* (2006.01)
(52) U.S. Cl. ........................ 250/292; 250/287; 250/288
(58) Field of Classification Search ................ 250/281, 250/282, 283, 287, 292
See application file for complete search history.

(56) References Cited

U.S. PATENT DOCUMENTS

| | | | | |
|---|---|---|---|---|
| 5,118,950 | A * | 6/1992 | Bahns et al. ................. 250/424 |
| 5,248,883 | A * | 9/1993 | Brewer et al. ............... 250/292 |
| 5,379,000 | A * | 1/1995 | Brewer et al. ................. 331/3 |
| 5,679,950 | A * | 10/1997 | Baba et al. ................. 250/281 |
| 5,783,824 | A * | 7/1998 | Baba et al. ................. 250/281 |
| 6,107,627 | A * | 8/2000 | Nakagawa et al. ......... 250/292 |
| 6,489,609 | B1 * | 12/2002 | Baba et al. ................. 250/282 |
| 6,566,651 | B1 * | 5/2003 | Baba et al. ................. 250/281 |
| 6,627,883 | B1 * | 9/2003 | Wang et al. ................ 250/292 |
| 6,737,641 | B1 * | 5/2004 | Kato .......................... 250/281 |
| 6,797,949 | B1 * | 9/2004 | Hashimoto et al. ......... 250/292 |
| 2003/0052264 | A1* | 3/2003 | Baba et al. ................. 250/281 |
| 2005/0139760 | A1* | 6/2005 | Wang et al. ................ 250/281 |
| 2005/0242279 | A1* | 11/2005 | Verentchikov .............. 250/287 |

OTHER PUBLICATIONS

R. E. March et al. "Review of the Development of the Quadrupole Ion Trap". Quadrupole Storage Mass Spectrometer, pp. 6-7, 13, Wiley, 1989.
R. F. Wuerker et al. "Electrodynamic Containment of Charged Particles". Journal of Applied Physics 30(3):342-349, 441-442.
R. E. March et al. "Nonlinear Ion Traps". Practical Aspects of Ion-Trap Mass Spectrometry, CRC Press, Boca Raton, FL, vol. 2, pp. 153-166, 1995.
I.S. Gilmore et al. "Ion detection efficiency in SIMS: dependencies on energy, mass and composition for microchannel plates used in mass spectrometry". International Journal of Mass Spectrometry 202:217-229, 2000.

(Continued)

*Primary Examiner*—Nikita Wells
*Assistant Examiner*—Johnnie L. Smith, II
(74) *Attorney, Agent, or Firm*—Fish & Richardson P.C.

(57) ABSTRACT

A nanoparticle ion detector includes an ion trap that receives charged particles ejected from a mass selection device. A laser beam illuminates the particles to induce fluorescence, which is detected by the photon detector. Particles are periodically dumped from the ion trap. A mass spectrum of the charged particles can be obtained by comparing signals from the photon detector with the particle ejection characteristics of the mass selection device.

72 Claims, 8 Drawing Sheets

OTHER PUBLICATIONS

R. E. March et al. "Quadrupole ion trap mass spectrometry: a view at the turn of the century". International Journal of Mass Spectrometry 200:285-312, 2000.

U. P. Schlunegger et al. "Frequency Scan for the Analysis of High Mass Ions Generated by Matrix-assisted Laser Desorption/Ionization in a Paul Trap". Rapid Communications in Mass Spectrometry 13:1792-1796, 1999.

S. Berkenkamp et al. "Infrared MALDI Mass Spectrometry. of Large Nucleic Acids". Science 281:260-262, Jul. 10, 1998.

M. A. Park et al. "An Inductive Detector for Time-of-flight Mass Spectrometry". Rapid Communications in Mass Spectrometry 8:317-322, 1994.

D. C. Imrie et al. "A Faraday Cup Detector for High-mass Ions in Matrix-assisted Laser Desorption/Ionization Time-of-flight Mass Spectrometry". Rapid Communications in Mass Spectrometry 9:1293-1296; 1995.

U. Bahr et al. "A charge detector for time-of-flight mass analysis of high mass ions produced by matrix-assisted laser desorption/ionization (MALDI)". International Journal of Mass Spectrometry and Ion Processes 153:9-21, 1996.

S. D. Fuerstenau et al. "Molecular Weight Determination of Megadalton DNA Electrospray Ions Using Charge Detection Time-of-flight Mass Spectrometry". Rapid Communication in Mass Spectrometry 9:1528-1538, 1995.

W. H. Benner. "A Gated Electrostatic Ion Trap To Repetitiously Measure the Charge and m/z of Large Electrospray Ions". Anal. Chem. 69:4162-4168, 1997.

J. C. Schultz et al. "Mass Determination of Megadalton-DNA Electrospray Ions Using Charge Detection Mass Spectrometry". J. Amer. Soc. Mass Spectrom. 9:305-313, 1998.

D. Twerenbold. "Biopolymer mass spectrometer with cryogenic particle detectors". Nuclear Instruments and Methods in Physics Research 370 A:253-255, 1996.

G. C. Hilton et al. "Impact energy measurement in time-of-flight mass spectrometry with cryogenic microcalorimeters". Nature 391:672-675, Feb. 12, 1998.

M. Frank et al. "Energy-Sensitive Cryogenic Detectors for High-Mass Biomolecule Mass Spectrometry". Mass Spectrometry Reviews 18:155-186, 1999.

M. Frank. "Mass spectrometry with cryogenic detectors". Nuclear Instruments and Methods in Physics Research 444 A:375-384, 2000.

Y. Cai et al. "Single-Particle Mass Spectrometry of Polystyrene Microspheres and Diamond Nanocrystals". Analytical Chemistry 74(1):232-238, Jan. 1, 2002.

Y. Cai et al. "Calibration of an audio-frequency ion trap mass spectrometer". International Journal of Mass Spectrometry 214:63-73, 2002.

H. C. Van de Hulst. "Conservation of Energy and Momentum". Light Scattering by Small Particles, pp. 11-12, Wiley 1957.

Y. Cai et al. "Ion Trap Mass Spectrometry of Fluorescently Labeled Nanoparticles". Analytical Chemistry, American Chemistry Society, Jan. 23, 2003, pp. A-G.

R. P. Haugland. "Molecular Probes: Material Safety Data Sheet". Handbook of Fluorescent Probes and Research Chemicals, 6th Edition, Molecular Probes, Eugene, 1996.

X. S. Xie et al. "Optical Studies of Single Molecules at Room Temperature". Annu. Rec. Phys. Chem 49:441-48, 1998.

E. J. Davis. "A History of Single Aerosol Particle Levitation". Aerosol Science and Technology 26(3):212-254, Mar. 1997.

W. B. Whitten et al. "Single-Molecule Detection Limits in Levitated Microdroplets". Anal. Chem. 63:1027-1031, 1991.

J. T. Khoury et al. "Pulsed Fluorescence Measurements of Trapped Molecular Ions with Zero Background Detection". J Am Soc Mass Spectrom 13:636-708, 2002.

Y. Cai et al. "Optical Detection and Charge-State Analysis of MALDI-Generated Particles with Molecular Masses Larger than 4MDa". Anal. Chem. 74:4434-4440, 2002.

J. Ting. "High-voltage current-feedback amplifier is speedy". EDN Magazine, pp. 136-137, Apr. 25, 2001.

C. Dass. "Comparison of Different Ionization Methods. Principles and Practices of Biological Mass Spectrometry". pp. 49, Wiley, 2001.

D. C. Schreimer et al. "Detection of High Molecular Weight Narrow Polydisperse Polymers up to 1.5 Million Daltons by MALDI Mass Spectrometry". Anal. Chem. 68:2721-2725, 1996.

M. Scalf et al. "Controlling Charge States of Large Ions". Science 283:194-197, Jan. 8, 1999.

L. Ding et al. "A simulation study of the digital ion trap mass spectrometer". International Journal of Mass Spectrometry 221:117-138, 2002.

J. Qin et al. "A Practical Ion Trap Mass Spectrometer for the Analysis of Peptides by Matrix-Assisted Laser Desorption/Ionization". Anal. Chem. 68:1784-1791, 1996.

C. Weil et al. "Multiparticle Simulation of Ion Injection into the Quadruple Ion Trap Under the Influence of Helium Buffer Gas Using Short Injection Times and DC Pulse Potentials". Rapid Communications in Mass Spectrometry 10:742-750, 1996.

V. M. Doroshenko et al. "Injection of Externally Generated Ions into an Increasing Trapping Field of a Quadrupole Ion Trap Mass Spectrometer". Journal of Mass Spectrometry 32:602-615, 1997.

L. He et al. "Simulation of External Ion Injection, Cooling and Extraction Processes with SIMION 6.0 for the Ion Trap/Reflectron Time-of-flight Mass Spectrometer". Rapid Communications in Mass Spectrometry 11:1467-1477, 1997.

S. T. Quarmby et al. "Fundamental studies of ion injection and trapping of electrosprayed ion on a quadrupole ion trap". International Journal of Mass Spectrometry 190/191:81-102, 1999.

S. Steiner et al. "Influence of Trapping Parameters on Ion Injection and Dissociation Efficiencies in a Quadrupole Mass Filter/Ion Trap Tandem Instrument". Journal of Mass Spectrometry 34:511-520, 1999.

K. Yoshinari. "Theoretical and numerical analysis of the behavior of ions injected into a quadrupole ion trap mass spectrometer". Rapid Communications in Mass Spectrometry 14:215-223, 2000.

A. D. Appelhans et al. "Measurement of external ion injection and trapping efficiency in the ion trap mass spectrometer and comparison with a predictive model". International Journal of Mass Spectrometry 216:269-284, 2002.

C. Marinach et al. "Simulation of ion beam and optimization of orthogonal tandem ion trap/reflector time-of-flight mass spectrometry". International Journal of Mass Spectrometry 213:45-62, 2002.

H.-P. Reiser et al. "Measurement of Kinetic Energies of Ions Ejected from a Quadrupole Ion Trap". International Journal of Mass Spectrometry and Ion Processes 106:237-247, 1991.

B. E. Dahneke. "Slip Correction Factors for Nonspherical Bodies-II Free Molecule Flow". Aerosol Science 4:147-161, 1973.

G. Hars et al. "Application of quadrupole ion trap for the accurate mass determination of submicron size charged particles". Journal of Applied Physics 77(9):4245-4250, May 1, 1995.

Y. Zerega et al. "A dual quadrupole ion trap mass spectrometer". International Journal of Mass Spectrometry 190/191:59-68, 1999.

M. A. Tito et al. "Electrospray Time-of-flight Mass Spectrometry of the Intact MS2 Virus Capsid". Journal of American Chemical Society 122:3550-3551, 2000.

A. A. Rostom et al. "Detection and selective dissociation of intact ribosomes in a mass spectrometer". PNAS 97(10):5185-5190, May 9, 2000.

S. D. Fuerstenau et al. "Mass Spectrometry in an Intact Virus". Angew. Chem. Int. Ed. 40(3): 542-544, 2001.

M. D. Barnes et al. "Detection of Single Rhodamine 6G Molecules in Levitated Microdroplets". Anal. Chem. 65:2360-2365, 1993.

S. Schlemmer et al. "Nondestructive high-resolution and absolute mass determination of single charged particles in a three-dimensional quadrupole trap". Journal of Applied Physics 90(10):5410-5418, Nov. 15, 2001.

S. Arnold et al. "Convertible electrodynamic levitator trap to quasielectrostatic levitator for microparticle nucleation studies". Review of Scientific Instruments 70(2): 1473-1477, Feb. 1999.

S.-C. Wang et al. "Plastic Microchip Electrophoresis with Analyte Velocity Modulation. Application to Fluorescence Background Rejection". Anal. Chem. 72:1448-1452, 2000.

J. R. Taylor et al. "Probing Specific Sequences on Single DNA Molecules with Bioconjugated Fluorescent Nanoparticles". Anal. Chem. 72:1979-1986, 2000.

* cited by examiner

NANOPARTICLE ION DETECTION

CROSS-REFERENCE TO RELATED APPLICATIONS

This application claims the benefit of U.S. Provisional Application No. 60/493,284 filed Aug. 7, 2003, the contents of which are herein incorporated by reference.

BACKGROUND

This description relates to nanoparticle ion detection.

Mass spectrometers can be used to determine the identities and quantities of components that make up a solid, gas, or liquid sample. A mass spectrometer may use the mass (m) to charge (z) ratios of ions to separate and analyze the ions. The ion charge represents the number of electric charges of the ion The ion mass may be expressed in atomic mass units or Daltons (Da). One type of mass spectrometer is the quadrupole ion trap mass spectrometer (QITMS), which can be used to analyze the masses of atomic, molecular, and cluster ions. A QITMS typically has a ring electrode and two end-cap electrodes. In operation, a time-varying voltage is applied between the ring electrode and the end-cap electrodes to create a time-varying electromagnetic field to confine the ions within a confinement region (a trap). By varying the frequency and/or amplitude of the time-varying voltage, the ions are selectively ejected from the ion trap based on their charge-to-mass ratios. To detect the ions that are ejected from the ion trap, a laser beam is directed towards the ions, and a photodetector detects light reflected from the ions.

SUMMARY

In general, in one aspect, the invention features a method that includes ejecting charged particles from a mass selection device, receiving the charged particles at an ion trap, illuminating the charged particles received at the ion trap to induce fluorescence, and detecting the fluorescence.

This and other aspects of the invention may include one or more of the following features.

The charged particles are ejected from the ion trap at selected time periods.

The charged particles are selectively ejected from the mass selection device based on their mass-to-charge ratios.

The mass selection device includes an ion trap. A first time-varying signal is applied to the ion trap of the mass selection device, and the frequency of the first time-varying signal is swept from a first frequency to a second frequency to cause particles having different mass-to-charge ratios to be ejected from the mass selection device at different frequencies of the first time-varying signal. The frequency of the first time-varying signal is scanned according to a non-linear function of time so that the mass-to-charge ratios of the particles ejected from the ion trap includes a linear function of time. A second time-varying signal is applied to the ion trap that receives the charged particles ejected from the mass selection device, and the frequency of the second time-varying signal is swept based on the sweeping of the frequency of the first time-varying signal.

A mass spectrum is generated by correlating the amount of fluorescence that is detected with characteristics of the mass selection device.

The characteristics of the mass selection device include a relationship between mass-to-charge ratios of particles ejected from the mass selection device and a time-varying control signal applied to the mass selection device.

A time-varying signal is applied to the ion trap that received the particles ejected from the mass selection device to generate a time-varying electromagnetic field to keep the charged particles within the ion trap.

The time-varying signal is turned off at selected time periods to remove substantially all of the particles from the ion trap.

A direct-current voltage signal is applied to the ion trap at selected time periods to induce an electromagnetic field that facilitates removal of the particles from the ion trap.

Detecting the fluorescence includes counting photons emitted from the particles.

A laser is directed to a sample to ionize and supply the particles to the mass selection device.

Electrospray ionization generates the charged particles and supplies the charged particles to the mass selection device.

Photo-ionization generates the charged particles and supplies the charged particles to the mass selection device.

Illuminating the charged particles includes directing a laser beam towards the charged particles, the laser beam having a wavelength selected to induce fluorescence from the charged particles.

The charged particles are tagged with fluorescent dye molecules.

The charged particles are tagged with more than one type of fluorescent dye molecules that emit fluorescence having different wavelengths.

The charged particles received at the second ion trap are illuminated by a light beam with components having different wavelengths that are selected to induce fluorescence having different wavelengths from the different types of fluorescent dye molecules.

A mass spectrum is generated for each group of particles tagged with a particular type of fluorescent dye molecules.

In general, in another aspect, the invention features a method that includes receiving charged particles at an ion trap, the charged particle traveling at a speed greater than 1 meter per second prior to being received by the ion trap, applying a trap driving signal to the ion trap to generate an electromagnetic field in the ion trap to cause the charged particles to be trapped within the ion trap, illuminating the charged particles received at the ion trap to induce fluorescence, and detecting the fluorescence emitted from the charged particles.

This and other aspects of the invention may include one or more of the following features. The charged particles are selectively ejected from a mass selection device based on mass-to-charge ratios of the charged particles, at least a portion of the particles ejected from the mass selection device being received by the ion trap.

In general, in another aspect, the invention features a method that includes applying a first time-varying voltage signal to a first ion trap that has charged particles, scanning a frequency of the first time-varying voltage signal from a first frequency to a second frequency to selectively eject the charged particles, applying a second time-varying voltage signal to a second ion trap that receives the charged particles ejected from the first ion trap, and scanning a frequency of the second time-varying voltage signal according to a predefined relationship to the frequency of the first time-varying voltage signal to tend to keep the charged particles received by the second ion trap in the second ion trap.

This and other aspects of the invention may include one or more of the following features.

The frequency of the second time-varying voltage signal is scanned so as to maintain a trap parameter ($q_z$) of the second ion trap substantially constant with respect to the particles received by the second ion trap.

The trap parameter $q_z$ is proportional to the amplitude of the second time-varying voltage signal and inversely proportional to the square of the frequency of the second time-varying voltage signal.

In general, in another aspect, the invention features a method that includes receiving charged particles at an ion trap, generate a time-varying electromagnetic field in the ion trap, and scanning a frequency of the time-varying electromagnetic field to tend to keep the charged particles in the ion trap.

This and other aspects of the invention may include one or more of the following features.

The charged particles have velocities that vary according to a predetermined function of time.

The scanning of the frequency of the time-varying electromagnetic field is based on the predetermined function of time.

In general, in another aspect, the invention features a method that includes selectively ejecting ions out of a mass selection device based on mass-to-charge ratios of the ions, using an ion trap to collect the ions ejected from the mass selection device, detecting light emitted from the ions in the ion trap to generate a detection signal, and correlating the detection signal with characteristics of the mass selection device to determine a mass spectrum on the ions in the ion trap.

This and other aspects of the invention may include one or more of the following features.

A laser is directed towards ions in the ion trap to induce fluorescence, and detecting light emitted from the ions includes detecting the fluorescence emitted from the ions.

In general, in another aspect, the invention features a method that includes using an ion trap to reduce speeds of charged particles selectively ejected from a mass selection device, and detecting fluorescence induced by a laser and emitted from the charged particles.

This and other aspects of the invention may include one or more of the following features.

The ions are either inherently fluorescent or are tagged with molecules that are fluorescent.

The mass selection device includes another ion trap.

The charged particles are selectively dumped from the ion trap.

Dumping of the charged particles from the ion trap is selected so that the fluorescence that is detected between two dumps represents an amount of charged particles having mass-to-charge ratios with a particular range.

In general, in another aspect, the invention features a method that includes receiving charged particles at an ion trap, applying a time-varying voltage signal to the ion trap to create a time-varying electromagnetic field in the ion trap, and selectively applying a direct-current voltage signal to the ion trap to cause the charged particles to be ejected from the ion trap.

This and other aspects of the invention may include one or more of the following features.

The polarity of the direct-current voltage depends on the polarity of the charges of the charged particles.

The time-varying voltage signal is selectively turned off when the direct-current voltage signal is applied to the ion trap.

In general, in another aspect, the invention features an apparatus that includes a mass selection device that selectively ejects charged particles, an ion trap to receive the charged particles ejected from the mass selection device, a light source to generate light to illuminate the charged particles in the ion trap to induce fluorescence, and a detector to detect the fluorescence.

This and other aspects of the invention may include one or more of the following features.

The ion trap includes a ring electrode, a first end-cap electrode, and a second end-cap electrode, the charged particles entering the ion trap through a hole in the first end-cap electrode and exiting the ion trap through a hole in the second end-cap electrode.

A signal generator generates a time-varying voltage signal, which when applied to the ion trap, generates a time-varying electromagnetic field in the ion trap to cause the particles ejected from the mass selection device to be trapped in the ion trap.

The detector includes a photomultiplier tube.

The charged particles are fluorescent or tagged with fluorescent dye molecules.

A laser source generates a laser beam that is directed towards the particles in the ion trap.

A signal generator generates a time-varying signal that is applied to the mass selection device, the signal generator scanning a frequency of the time-varying voltage signal from a first frequency to a second frequency during a measurement cycle to cause particles to be selectively ejected from the mass selection device based on mass-to-charge ratios of the particles. The signal generator scans the frequency of the time-varying voltage signal so that the frequency changes according to a non-linear function of time designed so that the particles ejected out of the ion trap during the measurement cycle have mass-to-charge ratios that vary as a linear function of time.

In general, in another aspect, the invention features an apparatus that includes an ion trap to receive charged particles selectively ejected out of a mass selection device based on mass-to-charge ratios of the particles, and a photodetector to detect light emitted from the particles in the ion trap.

This and other aspects of the invention may include one or more of the following features.

A laser generator generates a laser beam that is directed at the charged particles in the ion trap to induce fluorescence.

A circuit generates a control voltage that is applied to the ion trap to cause the ion trap to eject particles at selected times, the ejections of particles spaced apart for at least a specified time period to allow the photodetector to detect the light from the particles.

The laser generator generates a laser beam having a wavelength selected to induce fluorescence from the charged particles.

In general, in another aspect, the invention features an apparatus that includes an ion trap to receive charged particles traveling at a speed greater than 1 meter per second prior to being received by the ion trap, a signal generator to generate a trap driving signal that is applied to the ion trap to generate an electromagnetic field in the ion trap to cause the charged particles to be trapped within the ion trap, a laser generator to generate a laser beam to illuminate the charged particles received at the ion trap to induce fluorescence, and a detector to detect the fluorescence emitted from the charged particles.

This and other aspects of the invention may include one or more of the following features.

A mass selection device selectively ejects the charged particles based on mass-to-charge ratios of the charged particles, at least a portion of the particles ejected from the mass selection device being received by the ion trap.

In general, in another aspect, the invention features an apparatus that includes a first signal generator to generate a first time-varying voltage signal that is applied to a first ion trap having charged particles, the first signal generator scanning a frequency of the first time-varying voltage signal from a first frequency to a second frequency to selectively eject the charged particles from the first ion trap. A second signal generator generates a second time-varying voltage signal that is applied to a second ion trap that receives the charged particles ejected from the first ion trap, the second signal generator scanning a frequency of the second time-varying voltage signal according to a predefined relationship to the frequency of the first time-varying voltage signal to tend to keep the charged particles received by the second ion trap in the second ion trap.

This and other aspects of the invention may include one or more of the following features.

A third signal generator generates a third voltage signal that is selectively applied to the second ion trap to cause the charged particles in the second ion trap to be ejected from the second ion trap.

The third voltage signal includes a direct-current voltage signal.

The second signal generator scans the frequency of the second time-varying voltage signal so as to maintain a trap parameter ($q_z$) of the second ion trap substantially constant with respect to the particles received by the second ion trap.

The trap parameter $q_z$ is proportional to the amplitude of the second time-varying voltage signal and inversely proportional to the square of the frequency of the second time-varying voltage signal.

In general, in another aspect, the invention features an apparatus that includes an ion trap to receive charged particles traveling at different velocities at different time periods, and a signal generator to generate a time-varying control signal that is applied to the ion trap to generate a time-varying electromagnetic field in the ion trap, the signal generator scanning a frequency of the time-varying control signal to tend to keep the charged particles in the ion trap.

This and other aspects of the invention may include one or more of the following features.

The charged particles have velocities that vary according to a predetermined function of time.

The signal generator scans the frequency of the time-varying control signal based on the predetermined function of time.

In general, in another aspect, the invention features an apparatus that includes a mass selection device that selectively ejects ions based on mass-to-charge ratios of the ions, an ion trap that collects the ions ejected from the mass selection device, a detector to detect light emitted from the ions in the ion trap to generate a detection signal, and a data processor to correlate the detection signal with characteristics of the mass selection device to determine a mass spectrum on the ions in the ion trap.

This and other aspects of the invention may include one or more of the following features.

In general, in another aspect, the invention features an apparatus that includes an ion trap to reduce speeds of charged particles selectively ejected from a mass selection device, and a detector to detect fluorescence induced by a laser and emitted from the charged particles.

This and other aspects of the invention may include one or more of the following features.

The ions are either inherently fluorescent or are tagged with molecules that are fluorescent.

The charged particles are selectively dumped from the ion trap that reduced the speeds of the charged particles.

The dumping of the charged particles from the ion trap is selected so that the fluorescence that is detected between two dumps represents an amount of charged particles having mass-to-charge ratios with a particular range.

In general, in another aspect, the invention features an apparatus that includes an ion trap to receive charged particles, a first signal generator to generate a time-varying voltage signal that is applied to the ion trap to create a time-varying electromagnetic field in the ion trap, and a second signal generator to generate a dumping voltage signal that is selectively applied to the ion trap, the dumping voltage signal having a polarity based on a polarity of the charges of the charged particles, the dumping voltage signal causing the charged particles to be ejected from the ion trap.

This and other aspects of the invention may include one or more of the following features.

The dumping voltage signal includes a direct-current voltage signal.

The first signal generator selectively turns off the time-varying voltage signal when the dumping voltage signal is applied to the ion trap.

Other features and advantages of the invention are apparent from the following description, and from the claims.

DESCRIPTION

Nanoparticle Ion Detector

Figure 1:
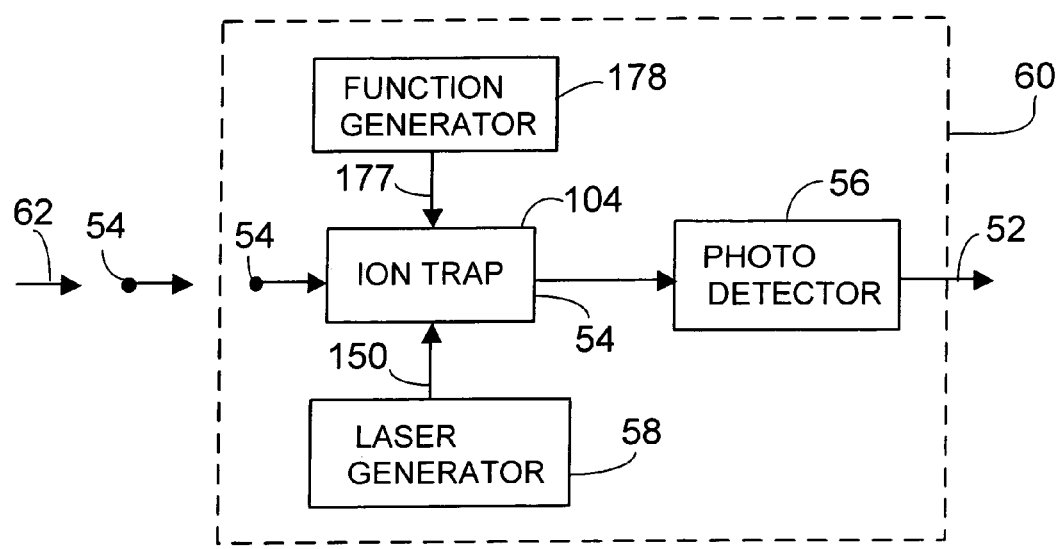
FIG. 1 shows a nanoparticle ion detector.

Referring to FIG. 1, a nano-particle ion detector 60 detects charged particles 54 traveling along a path 62. Detector 60 includes an ion trap 104, a function generator 178, a laser generator 58, and a photodetector 56. Function generator 178 generates a time-varying voltage signal 177 that is applied to the ion trap 104 to produce a time-varying electromagnetic field that traps the charged particles 54. A laser beam 150 (generated by the laser generator 58) is directed toward the particles to induce fluorescence, which is detected by a photodetector 56 to generate a detection signal 52.

Figure 2:
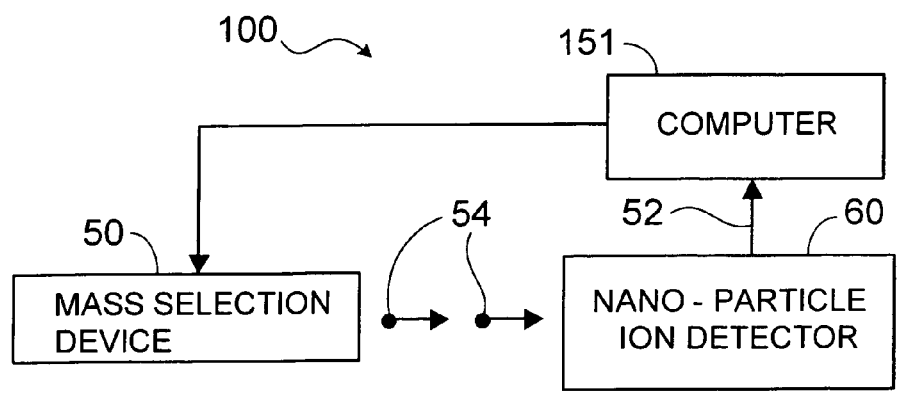
FIG. 2 shows a mass spectrometry system that includes the ion detector.

Referring to FIG. 2, in one example, the nanoparticle ion detector 60 is used with a mass selection device 50 and a computer 151 to form a mass spectrometry system 100. Mass selection device 50 ejects the charged particles 54 based on their mass-to-charge (m/z) ratios. Device 50 is triggered by the computer 151, which correlates the detection signal 52 with characteristics of the mass selection device 50 to determine a mass spectrum of the charged particles detected by the ion detector 60.

Particles ejected from the mass selection device 50 may have high speeds and may be difficult to detect. Ion trap 104 reduces the speeds of the particles and focuses the particles near the center of the ion trap 104 so that there is sufficient time for the particles to interact with the laser beam 150 to produce sufficient fluorescence that can be detected by the photodetector 56. In one example, the mass selection device 50 is designed so that mass-to-charge ratio of an ejected particle is a predefined function of time. Detecting the presence of the charged particles (by detecting fluorescence emitted from the particles) at different time periods provides information on the mass spectrum of the particles. By using the laser beam 150 to induce the particles to emit fluorescence, the nanoparticle ion detector 60 can detect particles having dimensions smaller than the wavelength of the laser beam 150. For example, the particles can be as small as a few nanometers. The nano-particle ion detector 60 can also be used to detect larger particles, such as particles having dimensions as large as 1 mm.

Dual Ion-Trap Mass Spectrometry System

Figure 3:
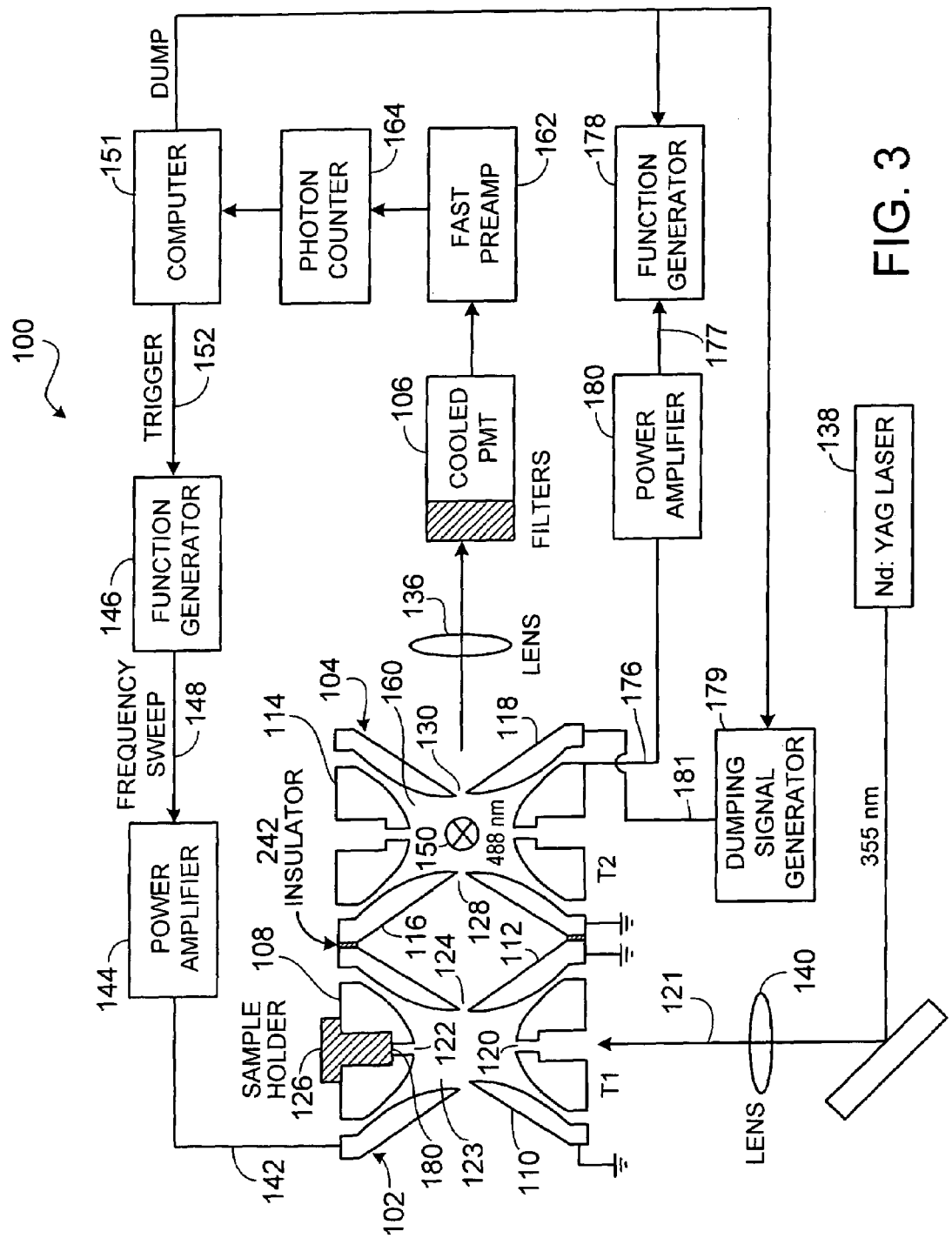
FIGS. 3 and 4 show a dual ion trap mass spectrometry system.
Figure 4:
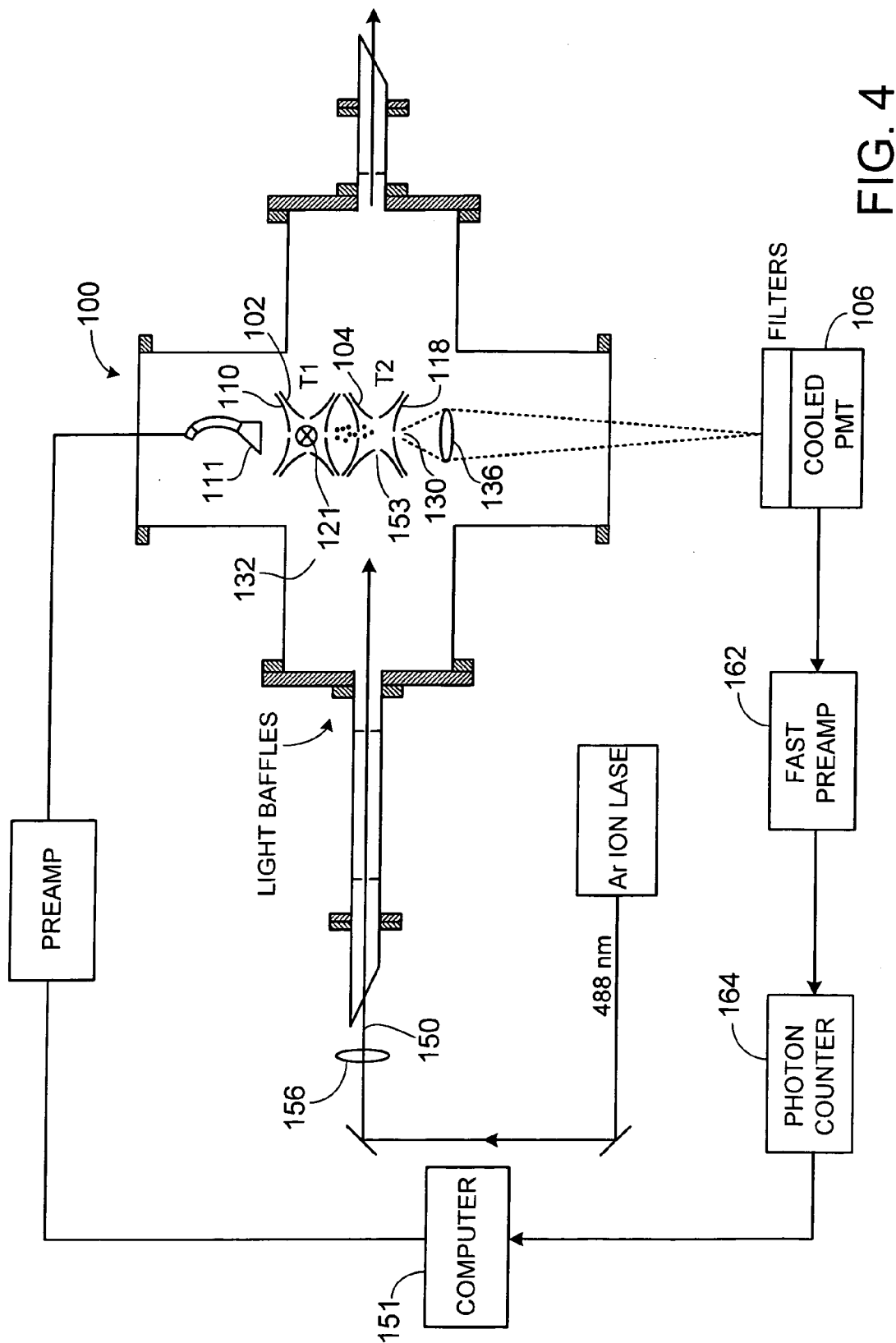

Referring to FIGS. 3 and 4, in one example, the mass spectrometry system 100 is a dual ion trap mass spectrometry system in which mass selection device 50 includes an ion trap 102. Ion trap 102 of the mass selection device 50 will be referred to as the first ion trap 102, and the ion trap 104 of the nano-particle ion detector 98 will be referred to as the second ion trap 104. Laser beam 150 is directed towards the charged particles in the second ion trap 104 to induce fluorescence, and a cooled photomultiplier tube 106 is used to detect the fluorescence.

Charged particles are periodically ejected from the second ion trap 104 at predetermined time intervals so that the amount of fluorescence detected during each interval is approximately proportional to the number of particles having a certain mass/charge ratio. A mass spectrum of the particles collected by the second ion trap 104 is obtained by comparing the fluorescence intensity detected by the photomultiplier tube 106 over a measurement period with known ion ejection characteristics of the first ion trap 102 over the measurement period.

FIGS. 3 and 4 show different views of the dual ion trap mass spectrometry system 100. In FIG. 3, a laser beam 121 enters the first ion trap 102 along a direction that is parallel to the plane of FIG. 3, and the laser beam 150 enters the second ion trap 104 along a direction that is perpendicular to the plane of FIG. 3. In FIG. 4, the laser beam 121 enters the first ion trap 102 along a direction that is perpendicular to the plane of FIG. 4, and the laser beam 150 enters the second ion trap along a direction that is parallel to the plane of FIG. 4.

The first and second ion traps 102 and 104 are mounted in a chamber 132 (FIG. 4). The first ion trap 102 can be, for example, a quadrupole ion trap, which includes a central, hyperbolic cross-section ring electrode 108 located between a first hyperbolic end-cap electrode 110 and a second hyperbolic end-cap electrode 112. Ring electrode 108 has holes 120 and 122 diametrically opposite to each other.

The dual ion trap mass spectrometer 100 can be used to measure particles having a wide range of sizes, including particles having dimensions greater than 10 nm, particles having masses greater than $10^6$ Dalton, and particles having mass/charge ratios greater than $10^6$ The charged particles can be inherently fluorescent (i.e., the particles themselves can emit fluorescence), or can be tagged with dye molecules that are fluorescent.

In one implementation, charged particles are generated in the first ion trap 102 using matrix-assisted laser desorption and ionization (MALDI). A stainless steel sample holder 126 holds a sample 180, which can be a matrix containing particles to be analyzed. A laser beam 121 passes through holes 120 and 122 to cause desorption and ionization of the particles, which subsequently enter into the first ion trap 102 through hole 122.

Charged particles are confined in the first ion trap 102 by applying a first trap driving signal 142 having a frequency $\Omega_1$ and an amplitude $V_{ac,1}$ to the ring electrode 108, with the end-cap electrodes 110 and 112 connected to a ground reference voltage. A function generator 146 outputs a frequency sweep signal 148, which is amplified by a power amplifier 144 to form the first trap driving signal 142. Function generator 146 sweeps the frequency of the first trap driving signal 142 over a range of frequencies based on the range of mass-to-charge ratios of the particles to be analyzed.

A computer 151 sends a trigger signal 152 to trigger the function generator 146 to start a frequency sweep. As the frequency $\Omega_1$ is scanned from, e.g., a higher frequency to a lower frequency (such as from 30 kHz to 200 Hz for particles having sizes ranging from 10 nm to 100 nm), the motions of charged particles having a succession of different mass-to-charge ratios become unstable and are ejected from the first ion trap 102 through a hole 124 of end-cap electrode 112. For a given geometry of the first ion trap 102 and a fixed voltage $V_{ac,1}$, the mass-to-charge ratio of the ions ejected from the first ion trap is a function of the frequency $\Omega_1$.

In general, a dimensionless parameter, called the "trap parameter" $q_z$, can be used to characterize the stability of the motion of a charged particle inside an ion trap:

$$q_z = \frac{4V_{ac}}{(m/z)r_0^2\Omega^2}, \quad \text{(Equ. 1)}$$

where $V_{ac}$ is amplitude of the trap driving signal (e.g., signal 142), $r_0$ is the distance from the center of the ion trap to the surface of the ring electrode (e.g., 108), and $\Omega$ is the frequency of the trap driving signal. When $q_z > 0.908$, the ion becomes unstable and is ejected out of the ion trap. Thus, particles of a given mass-to-charge ratio become unstable when $V_{ac}/\Omega^2$ reaches a certain value. If the voltage $V_{ac}$ is fixed, the frequency $\Omega$ determines the mass-to-charge ratio of the particles to be ejected.

Using Equ. 1, the mass-to-charge ratio (m/z) of a particle collected by the second ion trap 104 can be determined from parameters of the first trap driving signal 142 (i.e., $V_{ac}$, $r_0$, and $\Omega$), assuming $q_z = 0.908$.

Similar to the first ion trap 102, the second ion trap 104 can be, for example, a quadrupole ion trap, which has a central, hyperbolic cross-section, ring electrode 114 located between a first hyperbolic end-cap electrode 116 and a second hyperbolic end-cap electrode 118. End-cap electrode 116 has a hole 128 to allow ions ejected from the first ion trap 102 to enter the second ion trap 104. A second trap driving signal 176 having a frequency $\Omega_2$ and an amplitude $V_{ac,2}$ is applied to the ring electrode 114, and end-cap electrode 116 is grounded. End-cap electrode 118 is connected to a dumping signal generator 179, which will be described in more detail below. The particles are dumped from the second ion trap periodically (as described in more detail below) by applying a DC potential to the end-cap electrode 118 periodically.

The second trap driving signal 176 is generated by a function generator 178 and amplified by a power amplifier 180. Function generator 178 is controlled by computer 151. The frequency and amplitude of the second trap driving signal 176 are selected so that the ions ejected from the first ion trap 102 that are within the mass-to-charge ratio range sought to be analyzed are confined in the second ion trap 104.

The efficiency of the second ion trap 104 in trapping externally injected charged particles (which can be atomic or molecular particles) depends on the $q_z$ values of the ions entering the second ion trap 104. A trap ejection parameter $q_{eject}$ is used to represent the value of the trap parameter of a charged particle when the particle is ejected from an ion trap. When a particle ejected from the first ion trap 102 is trapped by the second ion trap 104, the trap ejection parameter $q_{eject,1}$, computed with respect to a particle ejected from the first ion trap 102, is approximately equal to the trap parameter $q_{z,2}$, computed with respect to a particle confined in the second ion trap 104. When the dimensions (e.g., $r_0$) of the first and second ion traps are the same, based on Equ. 1, the relationship between $q_{z,2}$ and $q_{eject,1}$ can be expressed as $$q_{z,2} \approx q_{eject,1} \frac{\Omega_1^2 V_{ac,2}}{\Omega_2^2 V_{ac,1}}. \quad \text{(Equ. 2)}$$

The trap driving voltages and frequencies of the first and second ion traps are selected so that $q_{z,2}$ is less than 0.908, so that ions ejected from the first ion trap 102 can enter and remain inside the second ion trap 104.

As the first driving voltage signal is swept over a range of frequency, the value $q_{z,2}$ changes. One way to keep $q_{z,2}$ substantially constant over the range of the frequency sweep is to sweep the frequency of the second trap simultaneously with the frequency of the first trap so that the trap parameter $q_{z,2}$ remains substantially constant. This can be achieved by using the computer 151 to synchronize the frequency sweeps of the first and second ion traps. In one example, the frequency sweeps of the first and second trap driving signals are synchronized to maintain $\Omega_2/\Omega_1 \approx 3$ and $V_{ac,1} = V_{ac,2}$ so that $q_{z,2} \approx 0.1$ during the frequency sweep.

A laser induced fluorescence method is used to detect the charged particles in the second ion trap 104. A laser beam 150 is directed through a hole 153 in ring electrode 114 towards the center of the second ion trap 104 where the charged particles are concentrated. Due to excitation from laser beam 150, the particles (or the dye molecules on the particles) become fluorescent and emit photons that pass through a hole 130 in end-cap electrode 118. Photons from the fluorescence are focused by a lens system 136 and detected by photomultiplier tube 106. Signals representing detected photons are amplified by a fast pre-amplifier 162 and counted by a photon counter 164. The count value from the photon counter 164 is sent to the computer 151 for further processing.

The photomultiplier tube 106 detects fluorescent light emitted from the charged particles, rather than light scattered from the particles. This allows the nanoparticle ion detector 60 to detect nanoparticles that have dimensions much smaller than the wavelength of the laser beam 150. If scattered light were used, the particles would have to have dimensions comparable to the wavelengths of the laser beam 150.

Because the second ion trap 104 collects nanoparticles near the center of the ion trap, a laser beam having a small cross section can accurately interrogate the nanoparticles. Because nanoparticles are small, the laser beam interrogating the nanoparticles needs to have sufficient intensity to induce fluorescence of sufficient intensity that can be detected by the photomultiplier tube. A laser source with a smaller power can be used by focusing the laser beam to have a smaller cross section and higher power. Without the second ion trap 104, the nanoparticles would spread out, and a laser beam with a larger cross section would be required, which would require a laser source with a higher power to induce fluorescence with sufficient intensity.

Damping and Dumping

The space 160 in the second ion trap 104 is filled with a buffer gas (e.g., He) to slow the injected particles and confine them in the center of the second ion trap 104 so that the particles can be interrogated by the focused laser beam 150. The period between the time that a particle enters the second ion trap 104 through hole 128 and the time that the particle settles near the center of the second ion trap 104 is referred to as the damping time. Reducing the damping time increases the signal-to-noise ratio as well as the mass resolution of the mass spectrum detected using the laser induced fluorescence method.

The charged particles are periodically ejected (or dumped) from the second ion trap 104 so that the count generated by the photon counter 164 for each mass-to-charge ratio is roughly proportional to the number of particles inside the second ion trap 104. If the particles are not ejected periodically, a particle that entered trap 104 would continuously emit photons and be counted multiple times. To eject the particles, the second trap driving signal 176 is temporarily turned off, and the DC dumping signal generator 179 generates a DC dumping signal 181 that is applied to the end-cap electrode 118 to induce the charged particles to exit the second ion trap 104 through hole 130. The polarity of the DC dumping signal 181 depends on the polarity of the charged particles. If the particles have positive charges, then the DC dumping signal 181 has a negative voltage, and vice versa.

Photon counter 164 counts the number of photons detected by photomultiplier tube 106 during a gate time (or gate period), and resets the counter during a dwell time (or dwell period). The second ion trap 104 is operated so that the dumping of particles in the second ion trap 104 coincides with the dwell time. By correlating the fluorescence intensity during a given measurement interval (represented by the count value) with the mass-to-charge ratio determined from Equ. 1 (which depends on the frequency of the trap driving signal at the given time), the amount of particles collected by the second ion trap 104 having a particular mass-to-charge ratio can be determined. This computation is performed in the computer 151. FIGS. 7A to 9 show examples of mass spectra obtained in this way.

The duration of the gate time and dwell time that are suitable for measuring a mass spectrum of a particular type of particles are determined as follows. The damping time of the particles in the second ion trap 104 is first determined by scanning the frequency of the first trap driving signal 142 to eject the particles to be analyzed, and counting the photons detected by photomultiplier tube 106. The count value will rise rapidly during a short period (which is called the rise time) and decay slowly afterwards. The rise time represents the damping time of the particles because the fluorescence grows stronger as more particles settle near the center of the second ion trap 104. The fluorescence peaks at a certain value when most of the particles are settled near the center of trap 104.

The damping time is affected by collisions between the charged particles and the buffer gas molecules in the second ion trap 104. The damping time is also affected by space charge effects, which means that, due to repulsion of charges particles, confining a larger number of charged particles near the center of trap 104 would take a longer time than confining a smaller number of charged particles. Reducing the trap driving voltage tends to increase the damping time because, when the trap driving voltage is decreased, the particles distribute themselves over a larger volume in space and take a longer time to settle. Since a lower damping time is preferred, it would be better to use a higher trap driving voltage for the second ion trap. As can be seen from Equ. 2, however, $V_{ac,2}$ cannot be selected to be so high that $q_{z,2}$ is greater than 0.908, which would cause the particles in the second ion trap 104 to be unstable and be ejected from the second ion trap 104. The amplitudes and frequencies of the first and second trap driving signals are selected so that $q_{z,2}$ remains less than 0.908.

Figure 5:
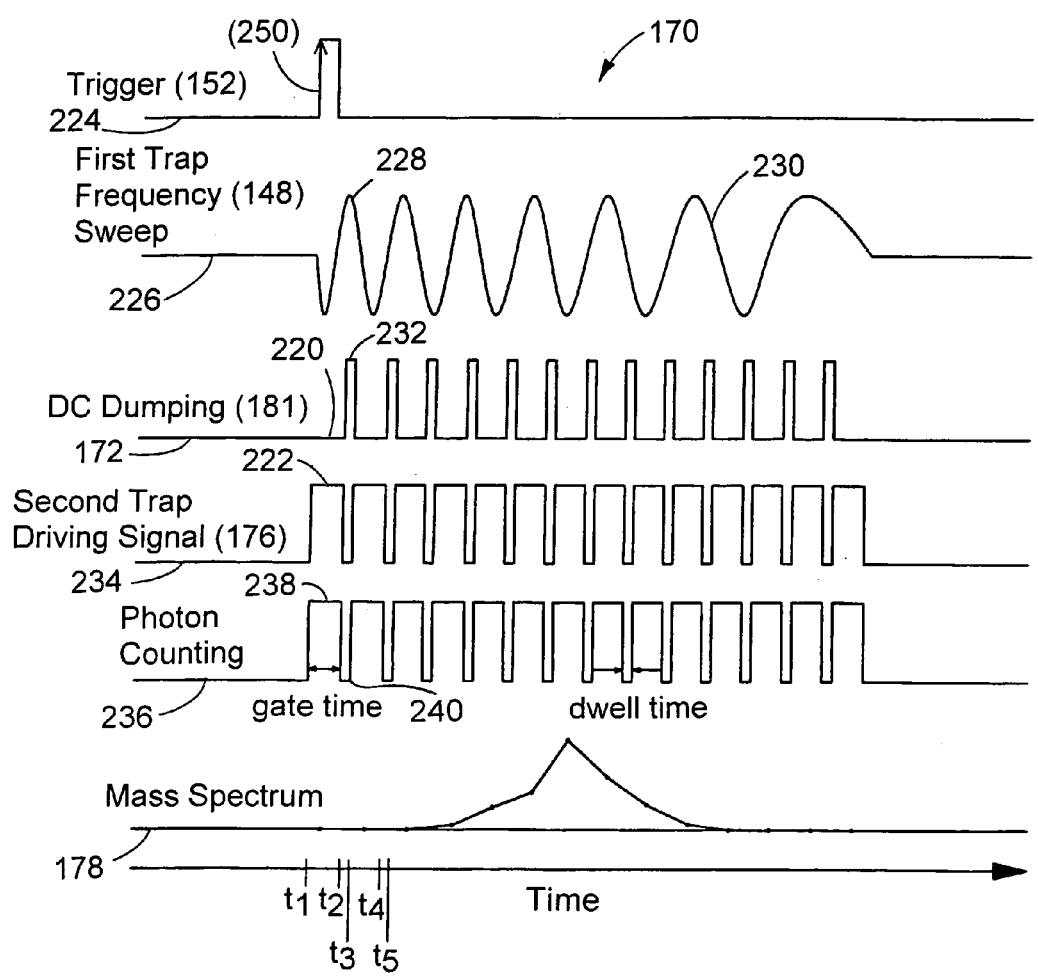
FIG. 5 shows timing diagrams.

Referring to FIG. 5, a graph 170 shows timing diagrams of various signals of system 100. Timing diagrams 224, 226, 172, 234, and 236 show the waveforms of the trigger signal 152, the frequency sweep signal 148, the DC dumping signal 181 (which includes periodic voltage pulses 232), the on-off times of the second trap driving signal 176, and the counting of photons from laser induced fluorescence, respectively.

In diagram 226, the vertical axis represents voltage amplitude. In diagram 236, a high (238) indicates a period when the photons emitted from particles in the second ion tap 104 are counted by photon counter 164, and a low (240) indicates a period when the counter is being reset and is not counting. The count values generated by photon counter 164 can be used to construct a mass spectrum 178 of the charged particles.

At time t1, the trigger signal 152 goes high (250) and triggers the frequency sweep signal 148. The DC dumping signal 181 is low (220), and the second trap driving signal 176 is turned on (222). This allows charged particles to accumulate inside the second ion trap 104. Photon counter 164 starts counting (238) photons from laser induced fluorescence.

At time t2 (where the period from t1 to t2 is the gate period of photon counter 164), the second trap driving signal 176 is turned off, and the DC dumping signal 181 is turned on. This causes the charged particles to be dumped from the second ion trap 104.

At time t3 (where the period from t2 to t3 is the dwell period of photon counter 164), the DC dumping signal 172 is turned off, and the second trap driving signal 176 is turned on. This causes charged particles of a different mass-to-charge ratio to start accumulating in second ion trap 104.

At time t4 (where the period from t3 to t4 is the gate time), the second trap driving signal 176 is turned off, and the DC dumping signal 172 is turned on. This causes the charged particles to be dumped from second ion trap 104, and so forth.

During the period t1 to t2, the charged particles that are accumulated in the second ion trap 104 have mass-to-charge ratios that correspond to the frequency of sweep signal 148 (see Equ. 1). The count value generated by photon counter 164 at time t2 roughly corresponds to the number of charged particles having a mass-to-charge ratio that is a function of the average frequency during the period from t1 to t2.

At time t3, the charged particles accumulated in second ion trap 104 during the period t1 to t2 have mostly been dumped. Thus, the count value generated by photon counter 164 at time t4 roughly corresponds to the number of charged particles having a mass-to-charge ratio that is a function of the average frequency between time t3 and t4.

As the first trap driving signal 142 is swept from a higher frequency (228) to a lower frequency (230), charged particles having different mass-to-charge ratios are selectively ejected from the first ion trap 102 (particles having smaller mass-to-charge ratios are ejected earlier, and particles having larger mass-to-charge ratios are ejected later). The photon counts accumulated by photon counter 164 as of the end of each gate time are used to generate a mass spectrum of the charged particles, as shown in diagram 178.

Implementation of the Dual Ion Trap Mass Spectrometry System

In one implementation, the first ion trap 102 and the second ion trap 104 are Paul traps from R. M. Jordan Company, Grass Valley, Calif. Both the first and the second ion traps have dimensions $r_0=10$ mm and $z_0=7.07$ mm, where $r_0$ is the radius of the ring electrode 108 (i.e., the distance between the center of the ion trap and the inner surface of the ring electrode), and $z_0$ is one-half the distance between the center of the end-cap electrodes 110 and 112. The first and second ion traps are separated by a 2-mm-thick Teflon insulator 242 with a circular aperture of 30 mm in diameter. Six holes were drilled in each ion trap (two on the end-cap electrodes and four on the ring electrode) for introduction of charged particles, entry of the MALDI laser beam 121, entry and exit of the probe laser beam 150, and collection of fluorescence. The holes in the first ion trap 102 have diameters equal to 3.1 mm. The holes on the end-cap and ring electrodes of the second ion trap 104 are 3.1 and 3.8 mm, respectively.

A Roots mechanical pump (not shown in the figure) is used to evacuate the vacuum chamber 132 to a base pressure of less than 1 mTorr. Helium gas is introduced into chamber 132 at a steady-state pressure p~50 mTorr.

Laser beam 121 is a pulsed laser having an energy of 5 mJ/pulse and a wavelength of 355 nm, and is generated by a frequency-tripled Nd:YAG laser 138 (model Surelite™, from Continuum®, Santa Clara, Calif.). Laser beam 121 is focused with a lens 140 having a focal length f=0.5 m, producing a spot size of about 1 mm in diameter on the sample 180. Function generator 146 is model DS345 Function & Arbitrary Waveform Generator, from Standard Research Systems, Sunnyvale, Calif., and is controlled by a data acquisition program, Labview, from National Instruments, Austin, Tex., running on computer 151.

Laser beam 150 has a wavelength of 488 nm, and is generated by an argon ion laser 154 (model Innova 90C, from Coherent Inc., Santa Clara, Calif.) having an operating power of 400 to 600 mW. Laser beam 150 is focused by a lens 156 having a focal length f=1 m, passes through light baffles 158 and a hole 153 on ring electrode 114 to form a spot size of approximately 200 μm in the trap center. Fluorescence emitted from the charged particles is focused by lens system 136, which has an f-number equal to 3 and a focal length f=38 mm. Photomultiplier tube 106 is a thermoelectrically cooled photomultiplier tube, model R943-02, from Hamamatsu Corporation, Bridgewater, N.J. Photon counter 164 is model SR400, from Stanford Research Systems.

As examples to show features and operations of system 100, yellow-green fluorescently labeled polystyrene beads (FluoSpheres, from Molecular Probes, Eugene, Oreg.) were analyzed. In one measurement, the polystyrene beads have sizes 27±4 nm. In another measurement, the polystyrene beads have sizes 110±8 nm. The 27 nm and 110 nm beads contain about 180 and 7400 fluorescein dye equivalents, respectively. The beads absorb light having a wavelength of 490 nm and emit light having a wavelength of 515 nm, with a quantum yield of about 30%.

To prepare the sample for MALDI, a solution containing the polystyrene beads was diluted with de-ionized water to a concentration on the order of $10^{13}$ particles/cm$^3$. Equal volumes of the sample (i.e., the diluted solution containing the polystyrene beads) and the matrix (which is a saturated solution of 3-hydroxypicolinic acid in 70/30 (v/v) acetonitrile/water solution) are combined and deposited on the sample holder 126. The sample holder 126 is mounted on the ring electrode 108 and fit into an upper ring electrode hole of the first ion trap 102.

The inner space of both the first and second ion traps are filled with He buffer gas having a pressure of p=50 mTorr. The He buffer gas in the first ion trap 102 assists trapping of the MALDI-generated charged particles. The He buffer gas in the second ion trap 104 assists trapping of the particles ejected from the first ion trap 102.

A channeltron 111, model H-305A, from De-Tech, is used for calibration of the first ion trap 102. The channeltron is operated at a voltage of −2350 V, and a deflection plate floated at −350 V is used to improve detection efficiency.

To acquire the mass spectra of 27 nm sized polystyrene beads, the first ion trap 102 is operated in an axial mass-selective instability mode by scanning the trap driving frequency ($\Omega_1/2\pi$) from 6k Hz to 500 Hz, at a constant amplitude ($V_{ac,1}$) of 200 V. This frequency scan mode avoided undesirable arcing among the three electrodes (ring electrode and end-cap electrodes) in the presence of the high-pressure buffer gas.

Before actually acquiring the mass spectra of the 27 nm polystyrene particles, measurements are made to determine the damping time of the 27 nm particles in the second ion trap 104. The first trap driving signal frequency $\Omega_1/2\pi$ was scanned from 6.0 kHz to 0.5 kHz in 200 ms to eject the 27 nm particles. The fluorescence signal detected by the photomultiplier tube 106 is shown in FIGS. 6A to 6B.

Figure 6A:
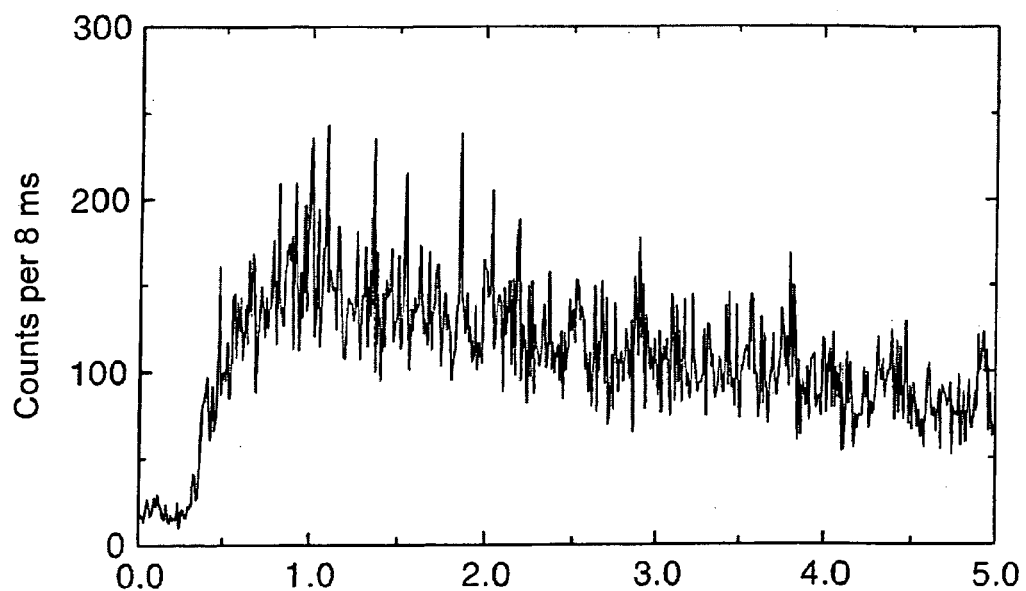
FIGS. 6A and 6B show signals from a photo detector.
Figure 6B:
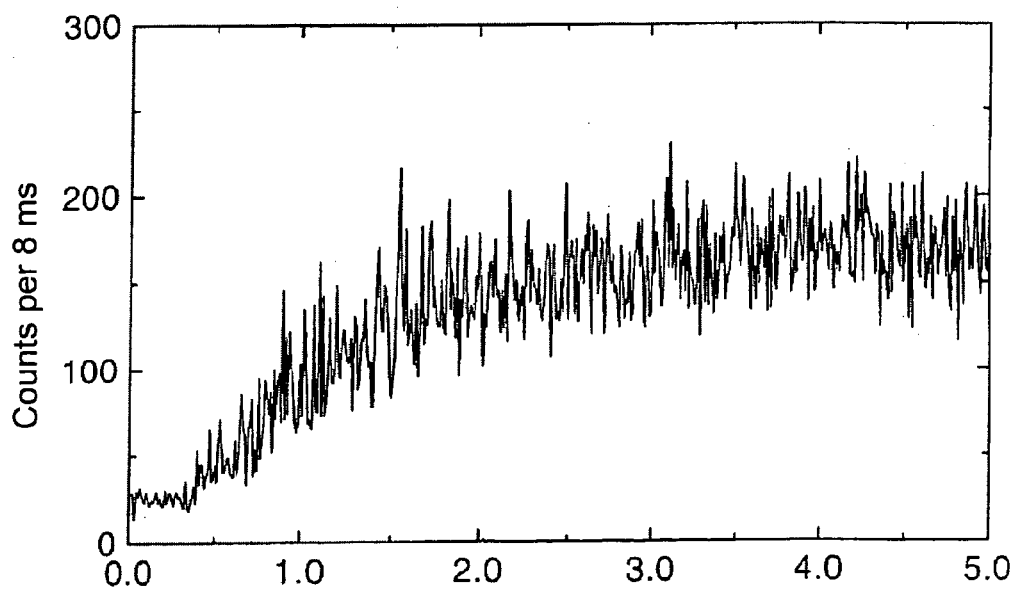

In each of FIGS. 6A to 6B, the second trap 104 was operated with a trap driving frequency $\Omega_2/2\pi$=6.0 kHz. The particles were ejected from the first ion trap 102 in 500 ms at a He buffer gas pressure of 50 mTorr. In FIGS. 6A and 6B, the second trap driving voltages were $V_{ac,2}$=160 V and $V_{ac,2}$=60 V, respectively. Comparing FIGS. 6A and 6B, the rise time increased as the amplitude of the second trap driving voltage decreased, from $\tau_d \approx 0.2$ second (in FIG. 6A) to $\tau_d \approx 1.0$ second (in FIG. 6B). Based on this result, a gate time of 200 ms in photon counting was chosen for data acquisition of the mass spectra of the 27 nm polystyrene particles, with the second trap driving voltage $V_{ac,2}$=160V.

The dumping time was selected to be 2 ms, and the DC dumping signal was selected to be −100 V. This is sufficient to cause most of the charged particles accumulated in the second ion trap 104 to be ejected from the second ion trap so as to prevent particle accumulation.

Figure 7A:
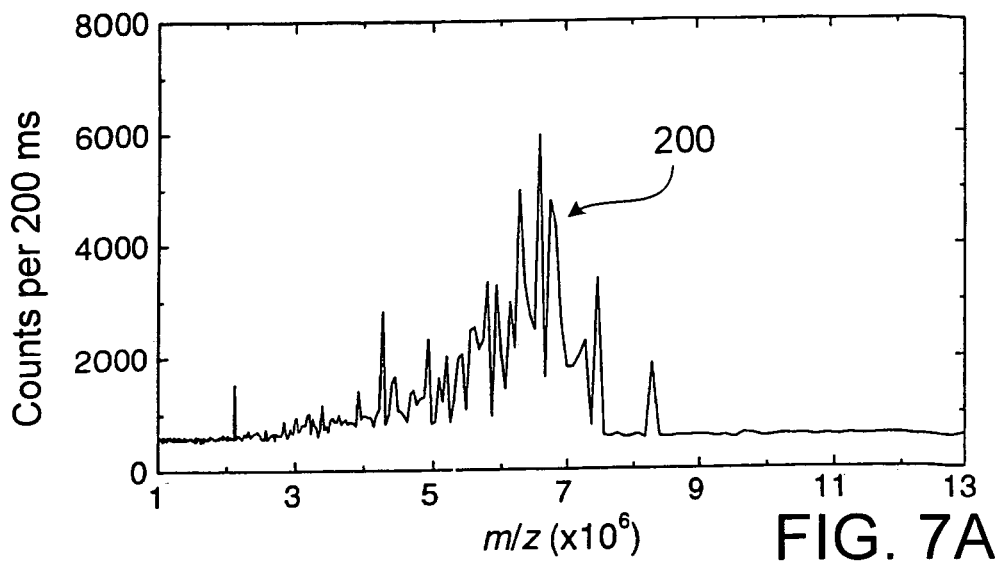
FIGS. 7A to 9 show mass spectra of particles.

FIG. 7A shows a single-scan mass spectrum 200 of the 27 nm polystyrene beads, which have a mean molecular mass of 6.5 MDa. A single-scan mass spectrum means that the mass spectrum was determined from measurements obtained from a single frequency sweep of the first trap driving signal 142. Irregular features are seen to spread over a range m/z=$2 \times 10^6$ to $9 \times 10^6$.

Figure 7B:
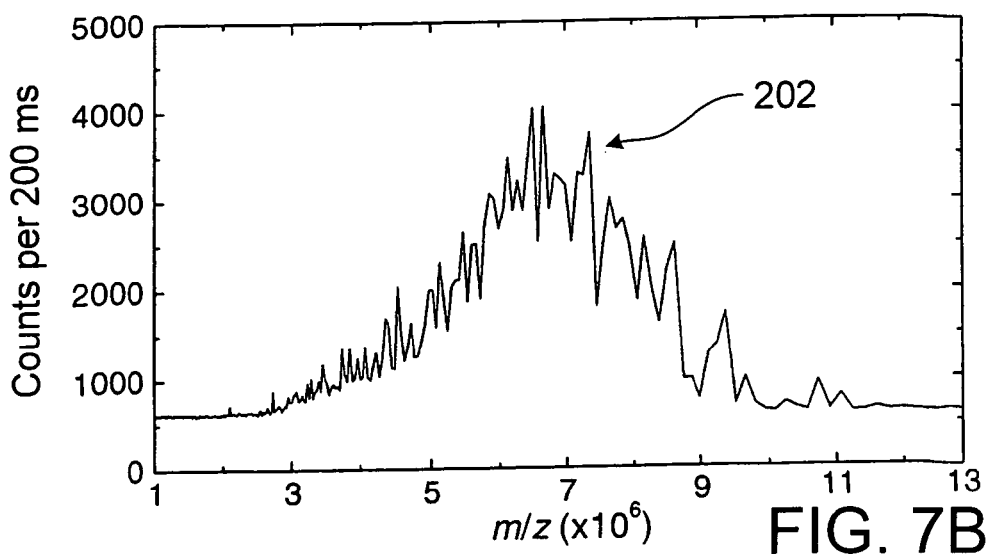

FIG. 7B shows a mass spectrum 202 obtained by accumulating the results from ten single-scan mass spectra. The mass spectrum 202 has a profile that is smoother than the mass spectrum 200. The majority of the features in mass spectrum 202 are centered around m/z$\approx 6.5 \times 10^6$, suggesting that the spectrum mostly represents singly charged particles.

Based on previous measurements for 1 µm particles, the mass spectrum was calibrated using the point of ejection, $q_{eject,1} \approx 0.95$ (rather than 0.908).

In both FIGS. 7A and 7B, the second trap driving signal 176 has a frequency fixed at $\Omega_2/2\pi$=6.0 kHz.

Figure 7C:
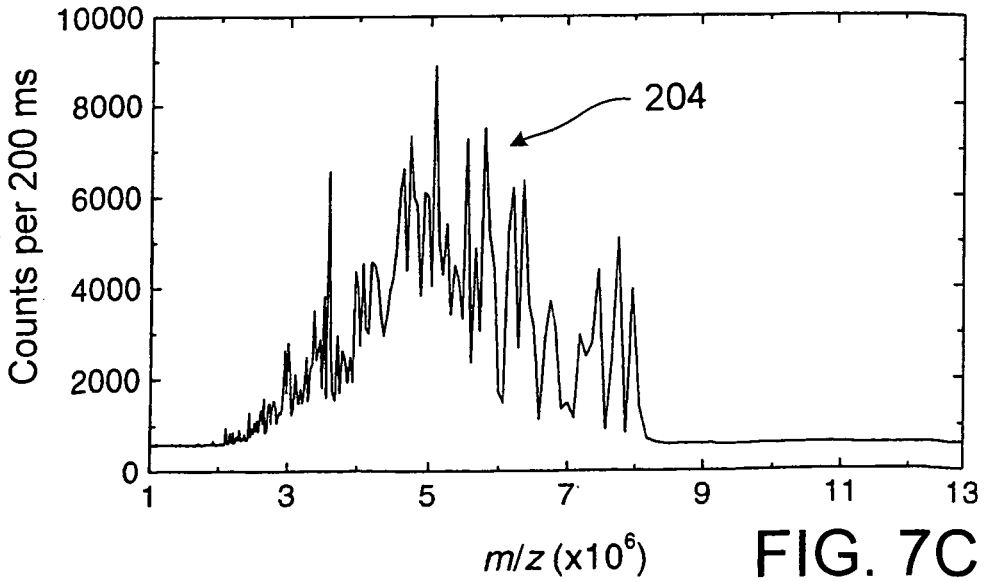

FIG. 7C shows a mass spectrum 204, also obtained by accumulating the results from ten single-scan mass spectra. For mass spectrum 204, the frequency $\Omega_2/2\pi$ of the second trap driving signal 176 is scanned simultaneously with the first trap driving signal 142 ($\Omega_1/2\pi$ is scanned from 6.0 kHz to 0.5 kHz, and $\Omega_2$=$3\Omega_1$), resulting in a substantially constant trap parameter $q_{z,2} \approx 0.1$. Comparing mass spectrum 204 with mass spectrum 202, the features of mass spectrum 204 is seen to shift to the lower m/z region. This shows that there are more doubly charged particles captured by the second ion trap 104 under the dynamic trapping condition (i.e., where the frequency of the second trap driving signal is also scanned) than the static trapping condition (i.e., where the second tap driving signal has a fixed frequency).

Figure 8A:
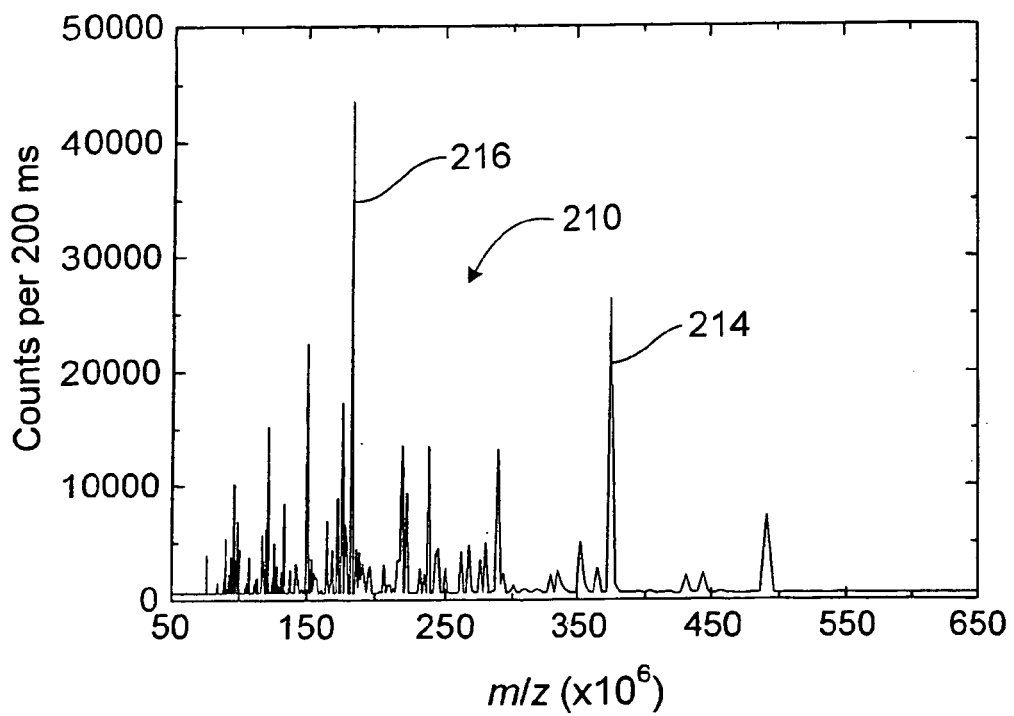

FIG. 8A shows a single-scan mass spectrum 210 of 110 nm particles that was acquired by sweeping the frequency of the first trap driving signal $\Omega_1/2\pi$ from 1.0 kHz to 0.2 kHz at $V_{ac,1}$=200 V. This trap driving signal causes particles with m/z in the range of $48 \times 10^6$ to $1200 \times 10^6$ to be ejected from the first ion trap 102. The 110 nm fluorescent spheres have a mean mass of 440 MDa, and a mass distribution of 350 to 543 MDa, due to size variations of ±8 nm. This suggests a m/z range of $(350-543) \times 10^6$ to $(58-91) \times 10^6$ for particles carrying 1 to 6 electric charges.

Figure 8B:
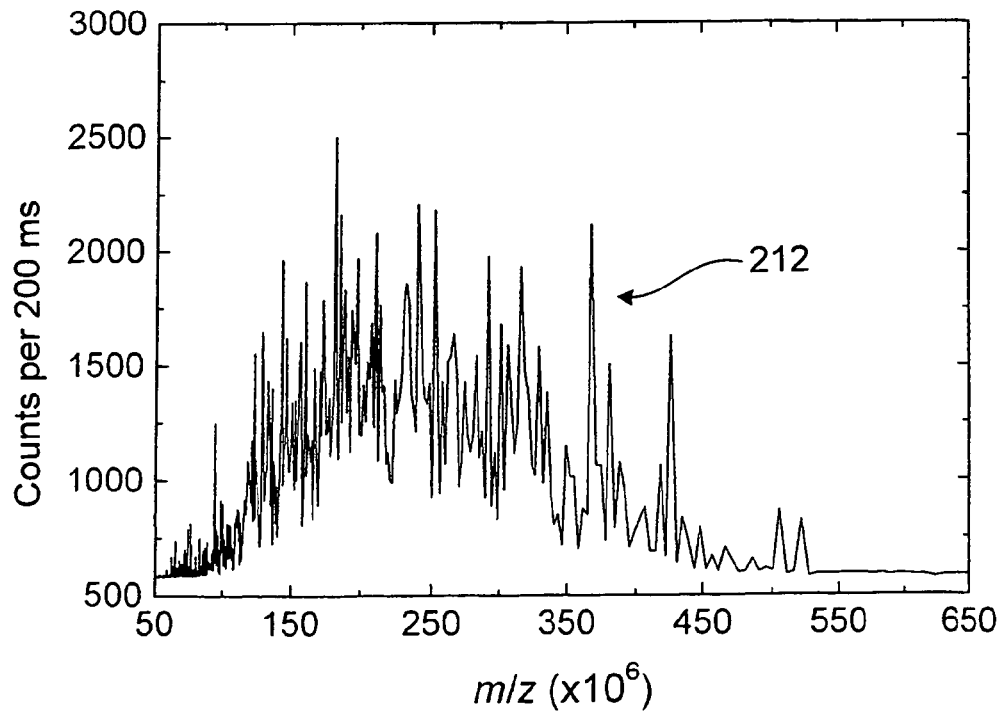

FIG. 8B shows a mass spectrum 212 obtained by accumulating the results from one hundred single-scan mass spectra. Mass spectrum 212 shows features from multiple charged particles. A comparison of mass spectra 212 and 204 (FIG. 7C) indicates that the 110 nm particles carry approximately twice the amount of the charges carried by the 27 nm particles.

It is estimated that for particles generated by MALDI and trapped in the first ion trap 102, roughly 10% of them will enter the second ion trap 104 upon the mass-selective axial ejection. This is because (1) equal portions of the particles are being ejected from the two end-cap electrodes of the first ion trap 102, (2) some of the ejected particles are lost during the particle transport from the first ion trap 102 to the second ion trap 104, and (3) a portion of the ejected particles cannot be captured by the second ion trap 104 due to phase mismatch. If there are initially 1000 charged particles in the first ion trap 102, about 100 charged particles would be detected using laser induced fluorescence method in the second ion trap 104 over the entire range of the frequency scan. The low particle density may explain why the spectra in FIGS. 7A to 8B have well-separated peaks (e.g., 214, 216), rather than having smooth continuous curves.

It is likely that the sharp and well-separated features (e.g., 214, 216) in FIG. 8A are derived from the individual 110 nm particles because each particle (FluoSphere) contains about 7400 fluorescein dye equivalents and can be easily detected. It is possible that particles fluorescently labeled with 10 fluorescein molecules or less can be detected using the process described above. Because particles of any size can be tagged with dye molecules, the spectral analysis range of the dual ion trap mass spectrometry system 100 is large.

The mass spectrometry system 100 can perform mass analysis of large biomolecules or bio-particles. As an example, system 100 was used to detect fluorescently labeled IgG (goat anti-mouse antibody), obtained from Molecular Probes. Each IgG was tagged with an average of 6.2 Alexa Fluor 488 dye molecules (having a mass of 643

Da), thereby having a total mass of about 150 kDa. The Alex Fluor 488 dye, which is spectrally similar to fluorescein, has absorption and emission maxima at 497 nm and 518 nm, respectively. The same lasers and light collection systems used for the 27-nm polystyrene spheres were used to measure the mass spectrum of the dye-labeled IgG molecules.

In the measurement of IgG, the gate time was selected to be 20 ms. The voltage of the DC dumping signal applied to the exit end-cap of the second ion trap 104 was −200 V. A single frequency sweep having 500 data points was completed in 11 seconds. Sinapinic acid was used as the laser desorption/ionization matrix.

Figure 9:
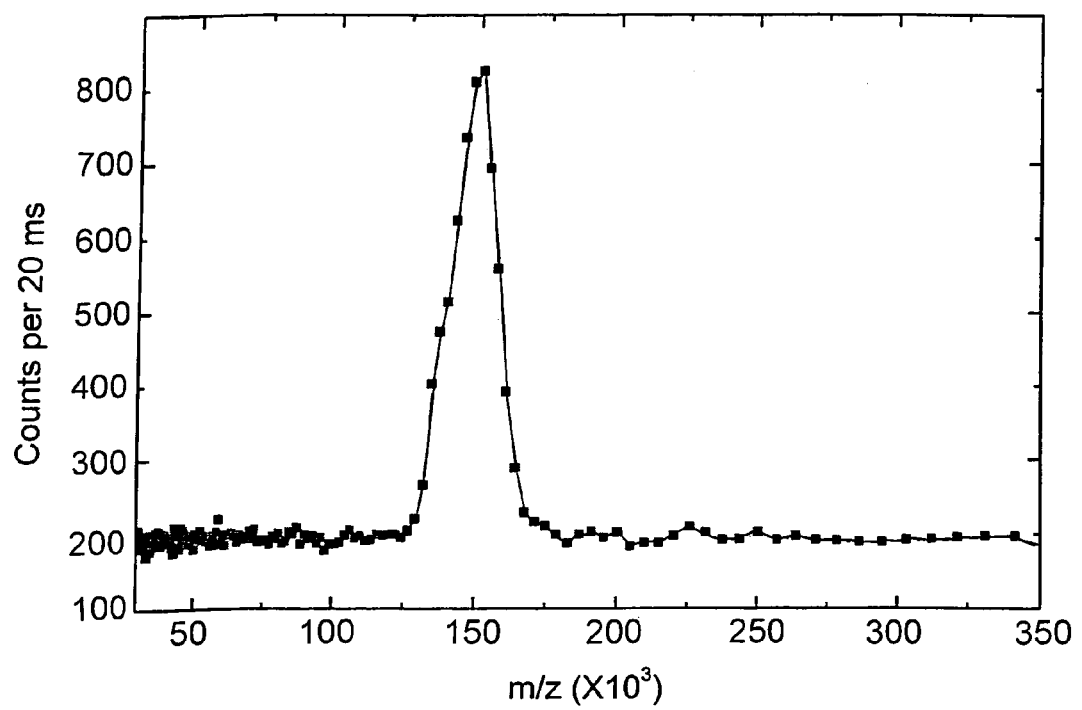

FIG. 9 shows a mass spectrum for the fluorescent IgG molecules. The mass spectrum was obtained by sweeping the driving frequency ($\Omega_1/2\pi$) of the first ion trap 102 from 40 kHz to 5 kHz at $V_{ac,1}$=200 V, with the second ion trap 104 operating in a dynamic trapping mode (i.e., the frequency of the second trap driving signal 176 is scanned simultaneously with the first trap driving signal 142), with $\Omega_2$=3 $\Omega$, and $V_{ac,2}$=160V. The laser power used to excite the dye molecules tagged on the IgG was 1.5 W and the damping time was 20 ms. A mass resolution of m/Δm=5 was achieved by accumulating data from 1 scan for singly charged IgG molecule at m/z≈1.5×10$^5$ with a signal-to-noise ratio greater than 10.

The mass spectrometry system 100 can be used to analyze large biological particles, such as viruses and other complex biomolecular assemblies. Such applications are practical since dye labeling has been routinely used in life science research. Prior to mass spectrometric analysis, the extent of dye labeling are quantified (i.e., the mass of the dye molecules on each particle are determined) by optical detection of the amount of dye molecules attached to the bio-particles. System 100 has an advantage that it does not require the particles to carry multiple charges for detection, even for large molecules.

Other embodiments are within the scope of the following claims.

For example, in FIG. 3, a DC dumping signal 182 (not shown) can be applied to the end-cap electrode 116 simultaneously with the application of signal 181 to electrode 118, the polarity of signal 181 being opposite to that of signal 182. This enhances the DC field that induces the particles to leave ion trap 104. The ions in the first ion trap 102 can be generated using electro-ionization (electrospray), or photo-spray methods.

The mass spectra shown in FIGS. 7A to 9 were acquired by sweeping the first trap driving frequency linearly at a low voltage (200 V) to avoid arcing of the electrodes in the presence of high-pressure (50 mTorr) He buffer gas. A nonlinear sweep of the frequency controlled by software running on computer 151 can be implemented to obtain a linear mass spectrum.

In one implementation, the first ion trap 102 is operated under the mass-selective instability mode by scanning the amplitude of the trap driving voltage with an AC voltage applied across the two end-cap electrodes. A differentially pumped region is established between the first and second ion traps. A He gas pulse is applied to the first ion trap to facilitate storage of particles in the first ion trap, and a steady flow of He buffer gas is maintained in the second ion trap 104 for damping purposes.

The detection sensitivity of spectrometer 100 can be increased by increasing the light collection efficiency using a lens system with an f-number equal to 1. The sensitivity can be further increased by using a more open trapping device to reduce the level of the background scattered laser light. A blue diode laser or a high-power LED (λ=473 nm) may substitute the Ar ion laser 154 as the light source to reduce cost. Sample-specific dye-labeling techniques can be used to differentiate nanoparticles among different samples through multicolor fluorescence spectroscopy with the aid of laser diodes.

What is claimed is:

1. A method comprising:
   selectively ejecting ions out of a mass selection device based on mass-to-charge ratios of the ions;
   using an ion trap to collect the ions ejected from the mass selection device;
   detecting light emitted from the ions in the ion trap to generate a detection signal; and
   correlating the detection signal with characteristics of the mass selection device to determine a mass spectrum on the ions in the ion trap.

2. The method of claim 1, further comprising directing a laser toward ions in the ion trap to induce fluorescence, and detecting light emitted from the ions comprises detecting the fluorescence emitted from the ions.

3. The method of claim 1 in which the mass selection device comprises an ion trap.

4. The method of claim 1, further comprising applying a first time-varying signal to the mass selection device, and sweeping a frequency of the first time-varying signal from a first frequency to a second frequency to cause particles having different mass-to-charge ratios to be ejected from the mass selection device at different frequencies of the first time-varying signal.

5. The method of claim 4 in which the frequency of the first time-varying signal is scanned according to a non-linear function of time so that the mass-to-charge ratios of the particles ejected from the mass selection device comprises a linear function of time.

6. The method of claim 4, further comprising applying a second time-varying signal to the ion trap that collects the ions ejected from the mass selection device, and sweeping a frequency of the second time-varying signal based on the sweeping of the frequency of the first time-varying signal.

7. The method of claim 1 in which at least some of the ions that are detected have dimensions larger than 10 nm.

8. The method of claim 1 in which at least some of the ions that are detected have masses larger than 1,000,000 Dalton.

9. The method of claim 1 in which at least some of the ions that are detected have mass/charge ratios larger than 1,000,000.

10. The method of claim 1, further comprising ejecting the ions from the ion trap at selected time periods.

11. The method of claim 10 in which ejecting the ions from the ion trap is selected so that the light that is detected between two ejections of the ions represents an amount of ions having mass-to-charge ratios within a particular range.

12. The method of claim 1, further comprising applying a time-varying voltage signal to the ion trap that collects the ions.

13. The method of claim 12, further comprising scanning a frequency of the time-varying voltage signal to tend to keep the ions collected by the ion trap in the ion trap.

14. The method of claim 13 in which the frequency of the time-varying voltage signal is scanned so as to maintain a trap parameter ($q_z$) of the ion trap substantially constant with respect to the particles collected by the ion trap.

15. The method of claim 14 in which the trap parameter $q_z$ is proportional to the amplitude of the time-varying voltage signal and inversely proportional to the square of the frequency of the time-varying voltage signal.

16. The method of claim 1 in which the ions ejected out of the mass selection device have velocities that vary according to a predetermined function of time.

17. The method of claim 16, further comprising generate a time-varying electromagnetic field in the ion trap, and scanning a frequency of the time-varying electromagnetic field to tend to keep the ions in the ion trap.

18. The method of claim 17 in which the scanning of the frequency of the time-varying electromagnetic field is based on the predetermined function of time.

19. The method of claim 1 in which the characteristics of the mass selection device comprise a relationship between mass-to-charge ratios of particles ejected from the mass selection device and a time-varying control signal applied to the mass selection device.

20. The method of claim 1, further comprising applying a time-varying signal to the ion trap to generate a time-varying electromagnetic field to keep the ions within the ion trap.

21. The method of claim 20, further comprising turning off the time-varying signal at selected time periods to remove substantially all of the ions from the ion trap.

22. The method of claim 20, further comprising applying a direct-current voltage signal to the ion trap at selected time periods to induce an electromagnetic field that facilitates removal of the ions from the ion trap.

23. The method of claim 1 in which detecting the fluorescence comprises counting photons emitted from the ions.

24. The method of claim 1, further comprising directing a laser to a sample to ionize particles and supplying the particles to the mass selection device.

25. The method of claim 1, further comprising using electrospray ionization to generate the ions and supplying the ions to the mass selection device.

26. The method of claim 1, further comprising using photo-ionization to generate the ions and supplying the ions to the mass selection device.

27. The method of claim 1, further comprising directing a laser beam towards the ions in the ion trap, the laser beam having a wavelength selected to induce fluorescence from the ions.

28. The method of claim 1, further comprising tagging the ions with fluorescent dye molecules.

29. The method of claim 1, further comprising tagging the ions with more than one type of fluorescent dye molecules that emit fluorescence having different wavelengths.

30. The method of claim 29, further comprising illuminating the ions collected at the ion trap using a light beam with components having different wavelengths that are selected to induce fluorescence having different wavelengths from the different types of fluorescent dye molecules.

31. The method of claim 30, further comprising generating a mass spectrum for each group of particles tagged with a particular type of fluorescent dye molecules.

32. The method of claim 1, further comprising selectively applying a direct-current voltage signal to the ion trap to cause the ions to be ejected from the ion trap.

33. The method of claim 32 in which the polarity of the direct-current voltage depends on the polarity of the charges of the ions.

34. The method of claim 33, further comprising applying a time-varying voltage signal to the ion trap to create a time-varying electromagnetic field in the ion trap.

35. The method of claim 34, further comprising selectively turning off the time-varying voltage signal when the direct-current voltage signal is applied to the ion trap.

36. An apparatus comprising:
a mass selection device to selectively eject charged particles based on mass-to-charge ratios of the charged particles;
an ion trap to receive the charged particles ejected from the mass selection device;
a detector to detect light emitted from the charged particles in the ion tap to generate a detection signal; and
a data processor to correlate the detection signal with characteristics of the mass selection device to determine a mass spectrum on the charged particles in The ion trap.

37. The apparatus of claim 36 in which the mass selection device comprises an ion trap.

38. The apparatus of claim 36 in which the ion trap comprises a ring electrode, a first end-cap electrode, and a second end-cap electrode, the charged particles entering the ion trap through a hole in the first end-cap electrode and exiting the ion trap through a hole in the second end-cap electrode.

39. The apparatus of claim 36, further comprising a signal generator to generate a time-varying voltage signal, which when applied to the ion trap, generates a time-varying electromagnetic field in The ion trap to cause the particles ejected from the mass selection device to be trapped in the ion trap.

40. The apparatus of claim 36 in which the detector comprises a photomultiplier tube.

41. The apparatus of claim 36 in which the charged particles are fluorescent.

42. The apparatus of claim 36 in which the charged particles are tagged with fluorescent dye molecules.

43. The method of claim 36 in which at least some of the charged particles that are detected have dimensions larger than 10 nm.

44. The method of claim 36 in which at least some of the charged particles that are detected have masses larger than 1,000,000 Dalton.

45. The method of claim 36 in which at least some of the charged particles that are detected have mass/charge ratios larger than 1,000,000.

46. The apparatus of claim 36, further comprising a laser source to generate a laser beam that is directed towards the particles in the ion trap.

47. The apparatus of claim 46 in which the laser beam has a wavelength selected to induce fluorescence from the charged particles.

48. The apparatus of claim 36, further comprising a signal generator to generate a time-varying signal that is applied to the mass selection device.

49. The apparatus of claim 48 in which the signal generator scans a frequency of the time-varying voltage signal from a first frequency to a second frequency during a measurement cycle to cause particles to be selectively ejected from the mass selection device based on mass-to-charge ratios of the particles.

50. The apparatus of claim 48 in which the signal generator scans a frequency of the time-varying voltage signal so tat the frequency changes according to a non-linear function of time designed so that the particles ejected out of the mass selection device during the measurement cycle have mass-to-charge ratios that vary as a linear function of time.

51. The apparatus of claim 36, further comprising a circuit to generate a control voltage that is applied to the ion trap to cause the ion trap to eject particles at selected fines.

52. The apparatus of claim 51 in which the ejections of particles are spaced apart for at least a specified time period to allow the detector to detect the light from the particles.

53. The apparatus of claim 36, further comprising a signal generator to generate a voltage signal that is selectively applied to the ion trap to cause the charged particles in the ion trap to be ejected from the ion trap.

54. The apparatus of claim 53 in which the voltage signal comprises a direct-current voltage signal.

55. The apparatus of claim 36, further comprising a signal generator to generate a time-varying voltage signal that is applied to the ion trap that receives the charged particles.

56. The apparatus of claim 55 in which the signal generator scans a frequency of the time-varying voltage signal to tend to keep the charged particles received by the ion trap in the ion trap.

57. The apparatus of claim 55 in which the signal generator scans a frequency of the time-varying voltage signal so as to maintain a trap parameter ($q_z$) of the ion trap substantially constant with respect to the particles received by the ion trap.

58. The apparatus of claim 57 in which the trap parameter $q_z$ is proportional to the amplitude of the time-varying voltage signal and inversely proportional to the square of the frequency of the time-varying voltage signal.

59. The apparatus of claim 55 in which the charged particles ejected out of the mass selection device have velocities that vary according to a predetermined function of time.

60. The apparatus of claim 59 in which the signal generator scans the frequency of the time-varying control signal based on the predetermined function of time.

61. The apparatus of claim 36, further comprising
a first signal generator to generate a time-varying voltage signal that is applied to the ion trap to create a time-varying electromagnetic field in the ion trap, and
a second signal generator to generate a dumping voltage signal tat is selectively applied to the ion trap to cause the charged particles to be ejected from the ion trap.

62. The apparatus of claim 61 in which the first signal generator selectively turns off the time-varying voltage signal when the dumping voltage signal is applied to the ion trap.

63. An apparatus comprising;
mass selecting means for selectively ejecting charged particles based on mass-to-charge ratios of the charged particles;
an ion trap for receiving the charged particles elected from the mass selecting means;
detecting means for detecting light emitted from the charged particles in the ion trap to generate a detection signal; and
data processing means for correlating the detection signal with characteristics of the mass selecting means to determine a mass spectrum of the charged particles in the ion trap.

64. The apparatus of claim 63 in which the mass selecting means comprises an ion trap.

65. The apparatus of claim 63, Thither comprising a laser source to direct a laser beam towards the charged particles in the receiving means to induce fluorescence that is detected by the detecting means.

66. The apparatus of claim 63, further comprising a signal generator to generate a time-varying voltage signal that is applied to the receiving means.

67. The apparatus of claim 66 in which the time-varying voltage signal generates a time-varying electromagnetic field in the receiving means to cause the particles ejected from the mass selecting means to be trapped in the ion trap.

68. The apparatus of claim 63, further comprising a signal generator to generate a time-varying signal that is applied to the mass selecting means.

69. The apparatus of claim 68 in which the signal generator scans a frequency of the time-varying voltage signal from a first frequency to a second frequency during a measurement cycle to cause particles to be selectively ejected from the mass selecting means based on mass-to-charge ratios of the particles.

70. The apparatus of claim 68 in which the signal generator scans the frequency of the time-varying voltage signal so that the frequency changes according to a non-linear function of time designed so that the particles ejected out of the mass selecting device during the measurement cycle have mass-to-charge ratios that vary as a linear function of time.

71. The apparatus of claim 63 in which the detecting means a photomultiplier tube.

72. The apparatus of claim 63, further comprising
a first signal generator to generate a time-varying voltage signal that is applied to the receiving means to create a time-varying electromagnetic field in the receiving means, and
a second signal generator to generate a dumping voltage signal that is selectively applied to the receiving means to cause the charged particles to be ejected from the receiving means,
wherein the first signal generator selectively turns off the time-varying voltage signal when the dumping voltage signal is applied to the receiving means.

* * * * *